(12) United States Patent
Yang

(10) Patent No.: US 6,338,732 B1
(45) Date of Patent: Jan. 15, 2002

(54) IN-MARROW NAIL STRUCTURE

(76) Inventor: Cher-Chung Yang, No. 137, Sec. 2 Min-Tsu Rd., Tainan (TW)

(*) Notice: Subject to any disclaimer, the term of this patent is extended or adjusted under 35 U.S.C. 154(b) by 0 days.

(21) Appl. No.: 09/512,623

(22) Filed: Feb. 25, 2000

(51) Int. Cl.[7] ............................................. A61B 17/86
(52) U.S. Cl. .......................................... 606/62; 606/73
(58) Field of Search .............................. 606/60, 62, 63, 606/64, 65, 66, 67, 68, 72, 73; 411/389, 397, 392, 379, 380, 381

(56) References Cited

U.S. PATENT DOCUMENTS

| | | | |
|---|---|---|---|
| 4,175,555 A | * | 11/1979 | Herbert |
| 4,640,271 A | * | 2/1987 | Lower |
| 4,723,541 A | * | 2/1988 | Reese |
| 4,964,403 A | * | 10/1990 | Karas et al. .................. 606/60 |

\* cited by examiner

Primary Examiner—David O. Reip
(74) Attorney, Agent, or Firm—Bacon & Thomas (57) ABSTRACT

In-marrow nail structure including an in-marrow nail main body two ends of which are respectively disposed with a thread tip section and a thread tail section. A polished section is formed between the two ends. A nut is screwed on the thread tail section. The thread tip section has a tip and a large thread section for easily drilling into and engaging with the dense section of the skeleton. The length of the polished section occupies a larger part of the total length of the main body so that when thrust into the marrow, the polished section is easier to be align with the fractured portion of the skeleton. In practical pressurizing, the stress is evenly shared. The diameters of the thread tip section and the thread tail section of the main body are both larger than the diameter of the polished section so as to enhance the strength thereof. Therefore, the breakage due to the concentrated stress taking place on the adjoining sections of the thread section and the polished section of the main body can be avoided and a more firmly restoring and fixing effect is provided for the fractured skeleton so as to achieve a good curing effect.

2 Claims, 8 Drawing Sheets

IN-MARROW NAIL STRUCTURE

BACKGROUND OF THE INVENTION

The present invention relates to an in-marrow nail structure which has enhanced strength and the breakage taking place at the section where stress is concentrated is avoided. Therefore, a more firmly restoring and fixing effect is provided for the fractured skeleton and the possibility of complications is lowered and the recovering time is shortened and a good curing effect is achieved.

Figure 1A:
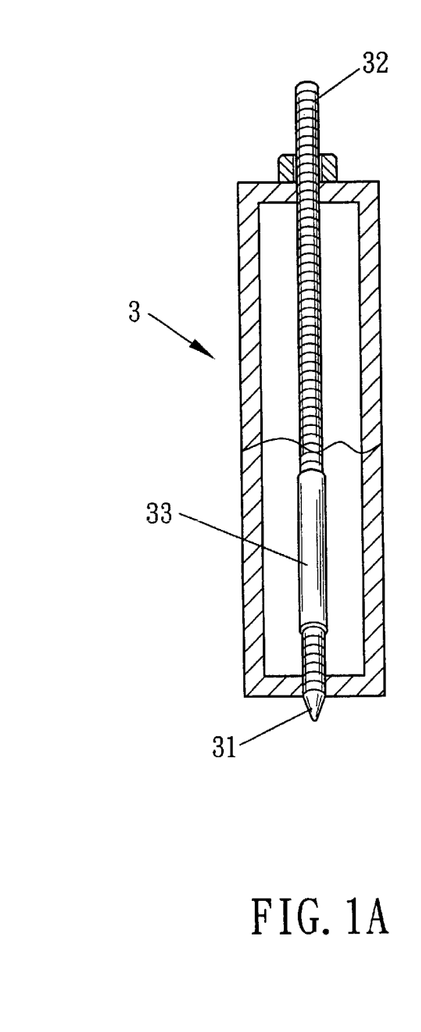
FIG. 1A is a sectional view showing a transverse fracture is pressurized by a conventional in-marrow nail.
Figure 1B:
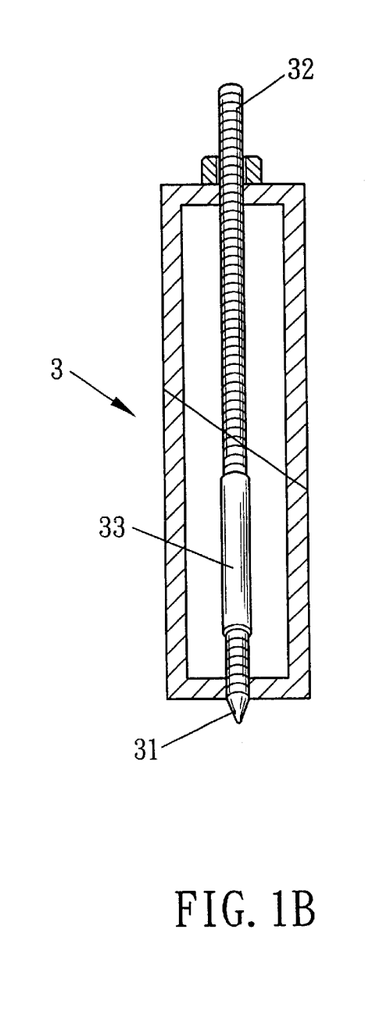
FIG. 1B is a sectional view showing an oblique fracture is pressurized by a conventional in-marrow nail.
Figures 1C, 1D:
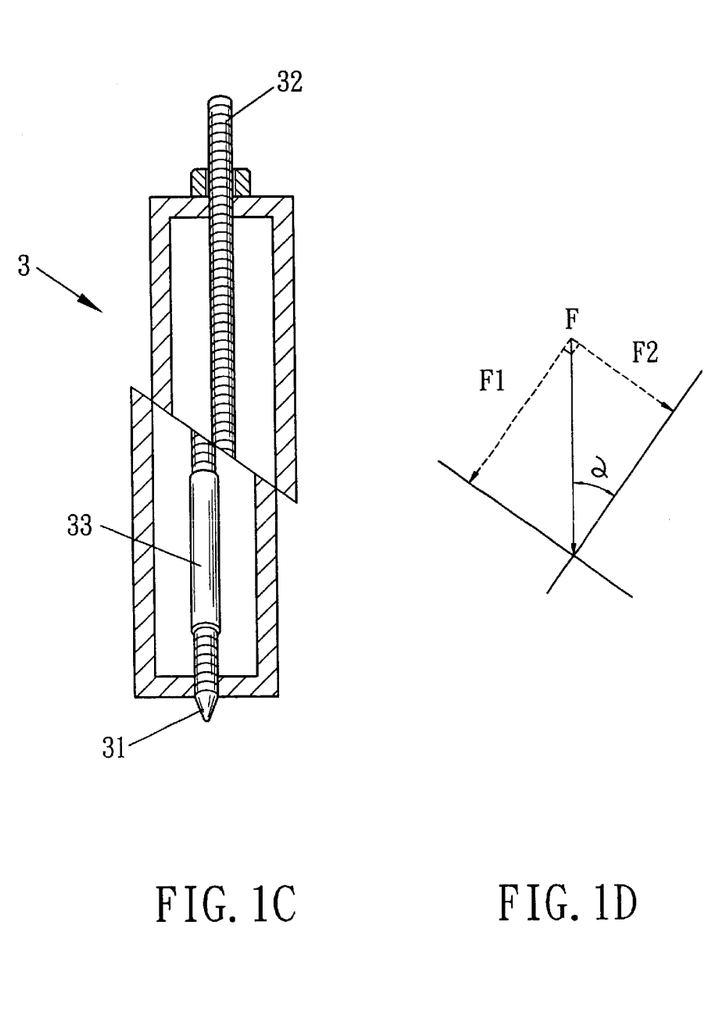
FIG. 1C is a sectional view showing an oblique fracture is pressurized by a conventional in-marrow nail, in which the nut is tightened and the fracture is displaced.
FIG. 1D is a force diagram of the fracture in pressurized state of FIG. 1C.
Figure 6:
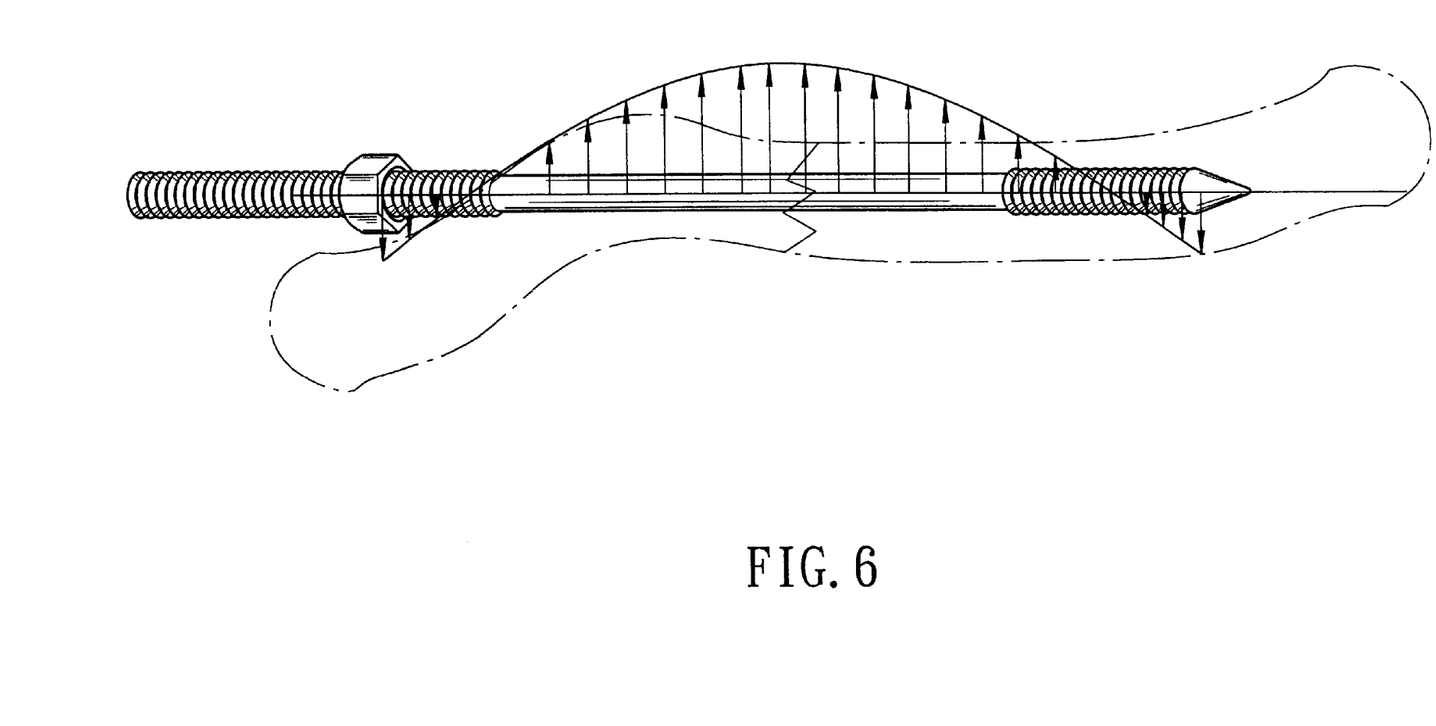
FIG. 6 is a force analysis diagram of the fracture in pressurized state.

In accidental injury, fracture of clavicle is one of the often seen injury. The existent treatments for fractured skeleton include: 1. Manual osteopathy co-used with sponge 8-bandage or plaster 8-bandage; and 2. Operation osteopathy and internal fixing such as in-marrow nail or steel board for internal fixing. Most of the cases can achieve good effect by way of manual osteopathy and 8-bandage. Only some of the cases necessitate operation treatment. Many fracture patterns or portions can be hardly treated by means of manual osteopathy to achieve a desired fixing effect. This prolongs recovering time. The operation osteopathy is able to achieve a firm fixing effect as well as a complete restoring effect with shortened recovering time. In order to enhance the chance of recovering and reduce the possibility of complications, the compressive in-marrow nail treatment is applied to the fractured skeleton. FIG. 1A shows a transverse stable fracture. Such fracture only needs a suitable pressure exerted onto the fractured skeleton to fix the fractured skeleton. Thereafter, the fractured skeleton will stably adjoin without deformation. This is the optimal fixing condition. FIGS. 1B and 1C show oblique fractures which are not stable. After pressurized and fixed, as shown in FIG. 1D, the component force will make the skeleton obliquely displace. Excessively large displacement will torque the fractured skeleton and lower the fixing and pressurizing effect. Therefore, left or right displacement will take place and it is impossible to stably pressurize and fix the fractured skeleton. Moreover, the main body 3 of the conventional in-marrow nail is not designed with thread pressurizing structure or the polished section 33 free from the thread of the in-marrow nail is very short. Therefore, it often takes place that when nailed into the fractured skeleton, the polished section can be hardly accurately aligned with the fractured portion and is very close to the adjoining section of the thread section and the polished section where the stress is concentrated. In addition, the diameter of the thread section is smaller than the diameter of the polished section 33. Therefore, in clinic use, breakage of the nail often takes place due to insufficient strength. The breakage is easiest to take place at the position near the adjoining section of the thread section and the polished section where the stress is concentrated. As a result, the broken nail will remain in the marrow and can be hardly taken out. In addition, with respect to fracture of clavicle trunk, the in-marrow nail is nailed into the fractured skeleton after the skeleton is restored. By way of the analysis in material dynamics, the middle of the transverse rod mainly suffers a bending force. The magnitude and direction of the force are as shown in FIG. 6. Two ends of the nail are inserted into the dense section of the clavicle and deemed as an integral body with the clavicle. The force application condition is as that two ends of the nail are tightly pinched by the thumbs and index-fingers of both hands. When suffering force, two ends are forced downward, while the middle is forced upward. Therefore, in the case that the effective length of the middle polished section is properly elongated, it is avoided that the section suffering greater stress is just positioned at the weaker section of the nail. This lowers the possibility of breakage of the nail.

SUMMARY OF THE INVENTION

It is therefore a primary object of the present invention to provide an improved in-marrow nail structure including an in-marrow nail main body two ends of which are respectively disposed with a thread tip section and a thread tail section. A polished section is formed between the two ends. The diameters of the thread tip section and the thread tail section of the main body are both larger than the diameter of the polished section and the effective length of the polished section is elongated so that the stress is evenly shared by respective portion of the main body during pressurizing. Therefore, the breakage due to the concentrated stress taking place on the adjoining sections of the thread section and the polished section of the main body can be avoided and a more firmly restoring and fixing effect is provided for the fractured skeleton.

It is a further object of the present invention to provide the above in-marrow nail structure in which the diameter of the thread tip section of the main body is slightly larger than the diameter of the thread tail section. Therefore, the thread tip section can easily firmly thrust into the dense section of the proximal end of the fractured skeleton to reduce the displacement caused by pressurizing. In addition, the thread tip section can directly preliminarily thrust through the marrow without using any other tool so that the operation procedure is simplified and the operation time is shortened.

It is still a further object of the present invention to provide the above in-marrow nail structure in which the diameter of the thread tail section is slightly smaller than the diameter of the thread tip section, whereby when the nut is tightened to press the distal end of the fractured skeleton, the diameter of the thread tail section is smaller than the diameter of the hole drilled by the thread tip section and the distal fractured section is slided and pressed toward the proximal fractured section and tightly mated therewith.

The present invention can be best understood through the following description and accompanying drawings wherein:

DETAILED DESCRIPTION OF THE PREFERRED EMBODIMENT

Figure 2:
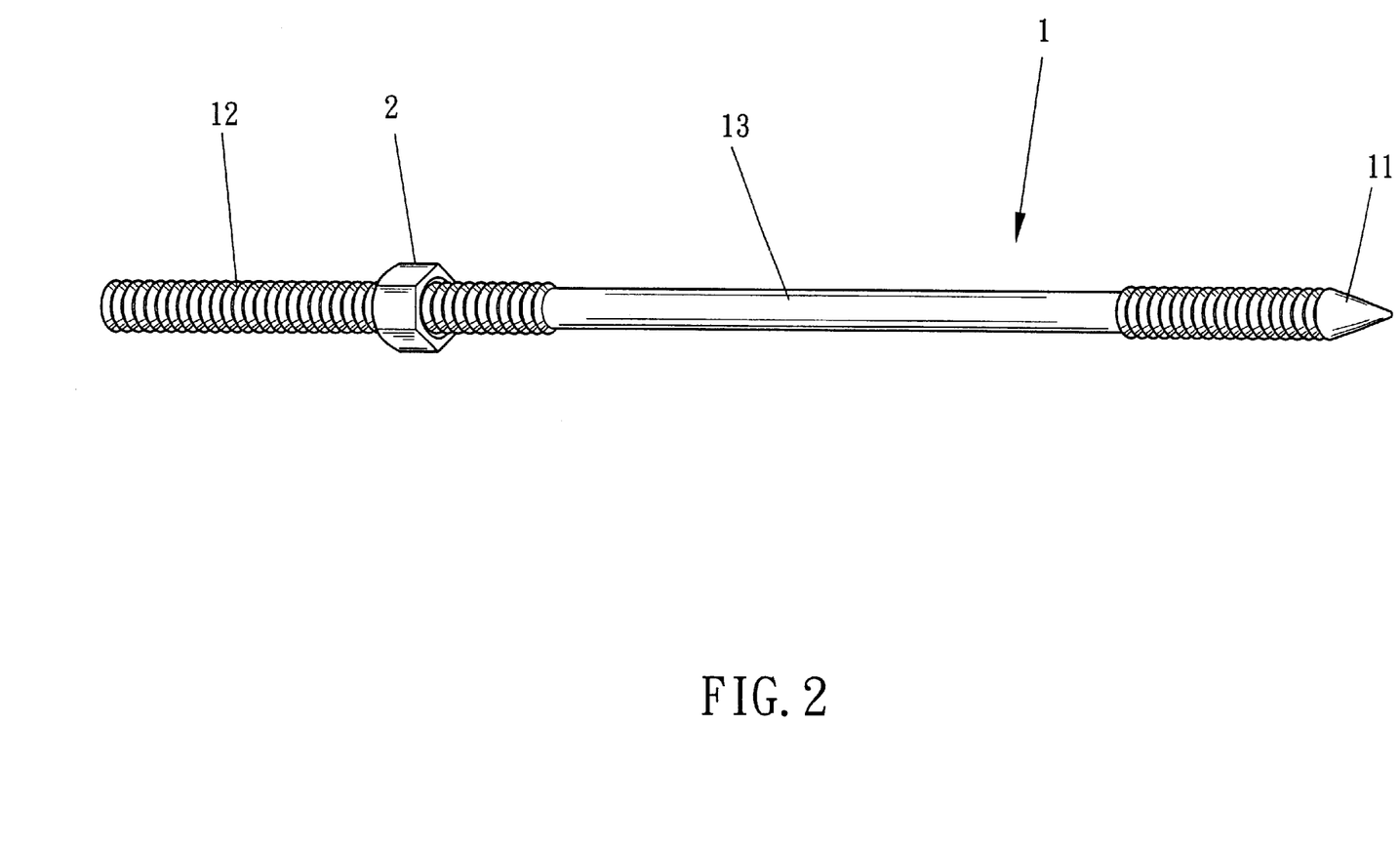
FIG. 2 is a perspective view of the in-marrow nail of the present invention.
Figure 3A:
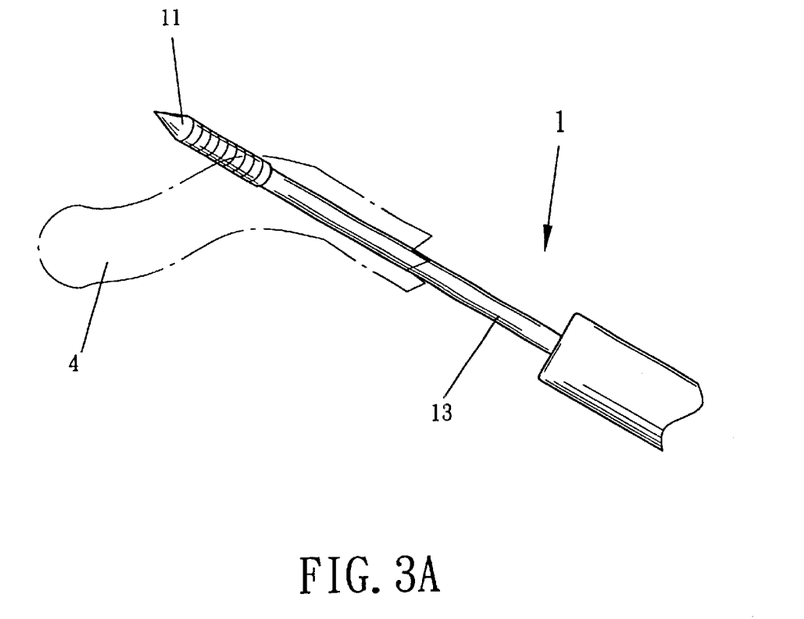
FIG. 3A shows that the in-marrow nail of the present invention is thrust through a distal marrow.
Figure 3B:
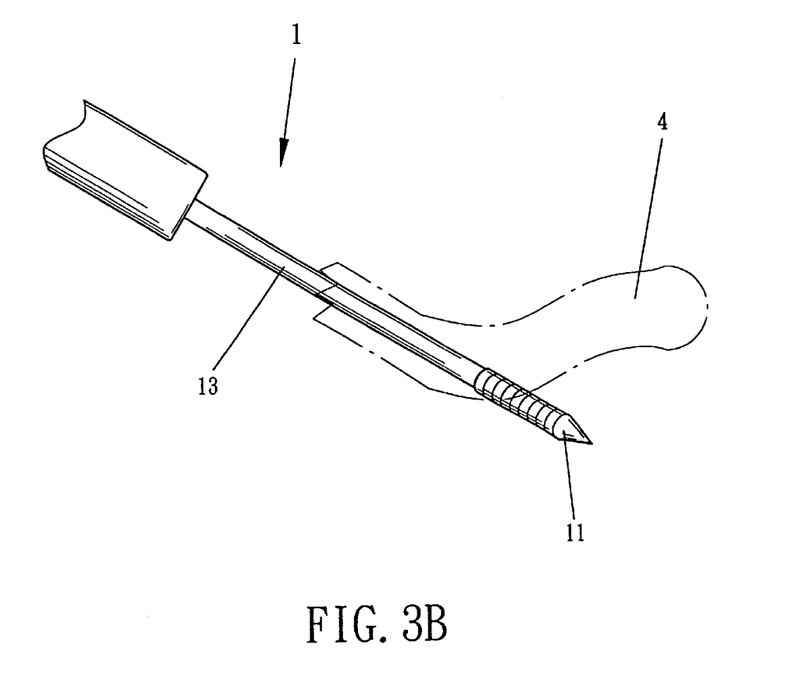
FIG. 3B shows that the in-marrow nail of the present invention is thrust through a proximal marrow.
Figure 3C:
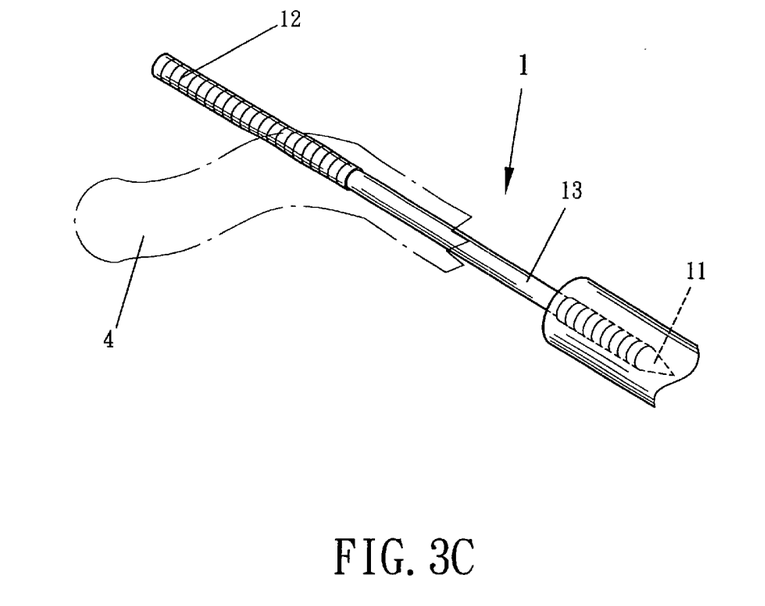
FIG. 3C shows that the tail end of the in-marrow nail of the present invention is reversely thrust through the distal marrow.
Figure 3D:
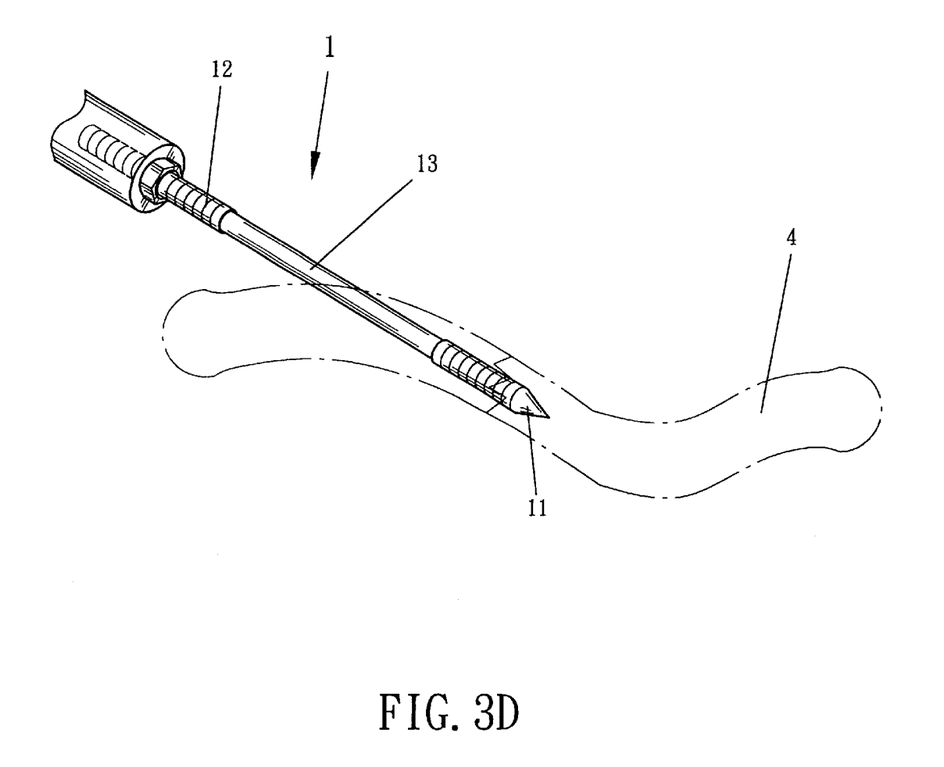
FIG. 3D shows that the in-marrow nail of the present invention is successively thrust through the marrow.
Figure 3E:
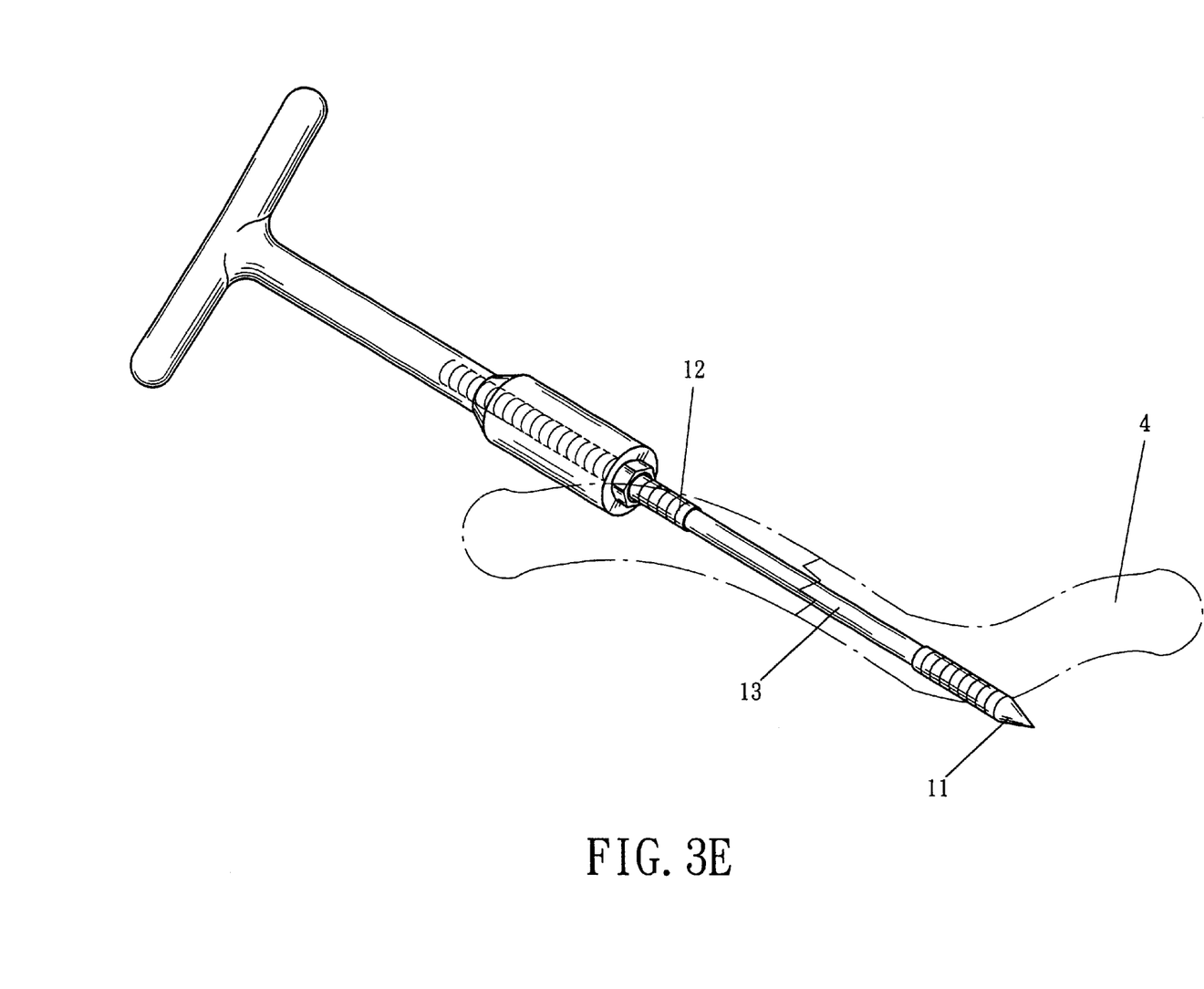
FIG. 3E shows that the nut of the in-marrow nail of the present invention is tightened to locate the nail.
Figure 4:
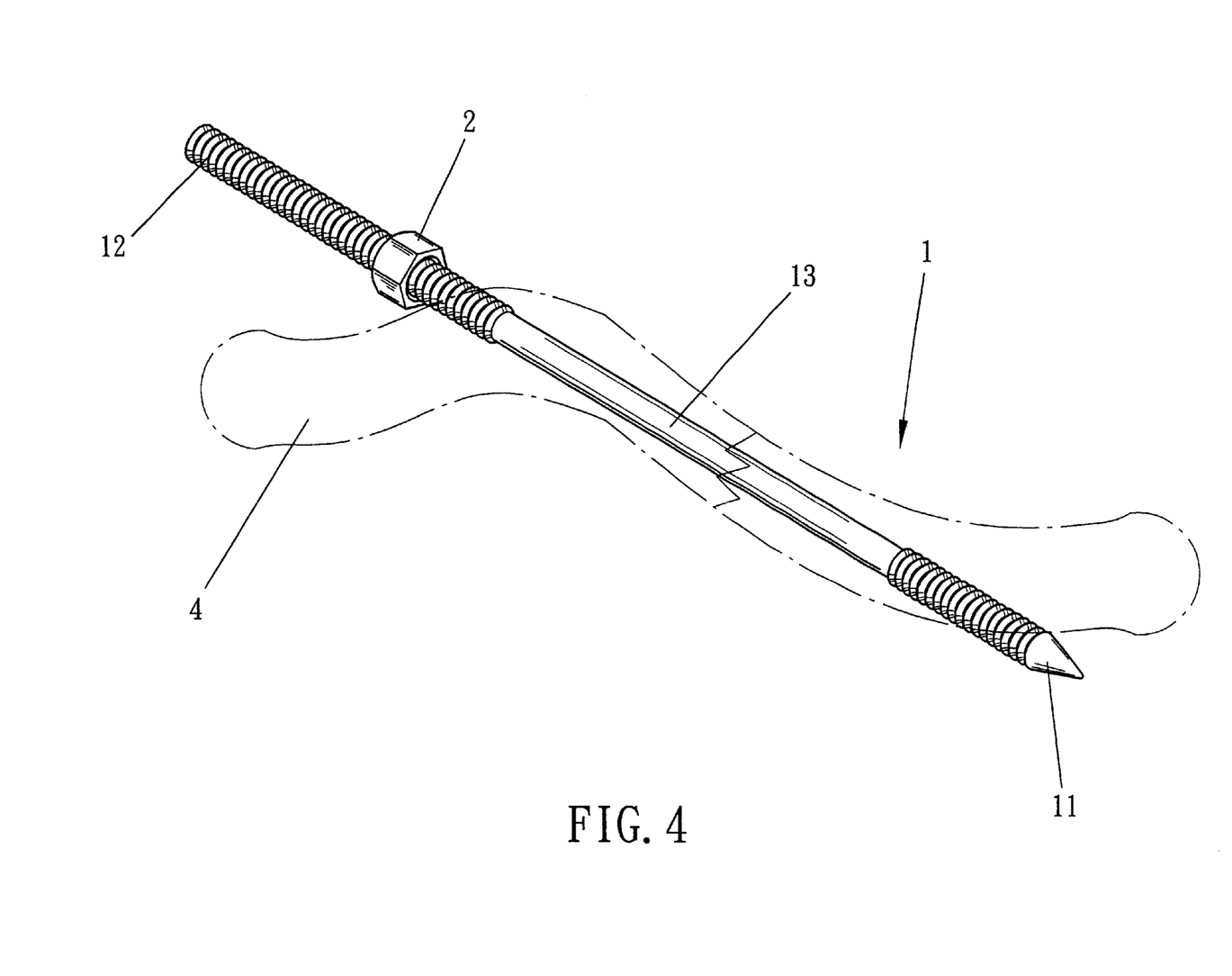
FIG. 4 shows an application of the in-marrow nail of the present invention.
Figure 5A:
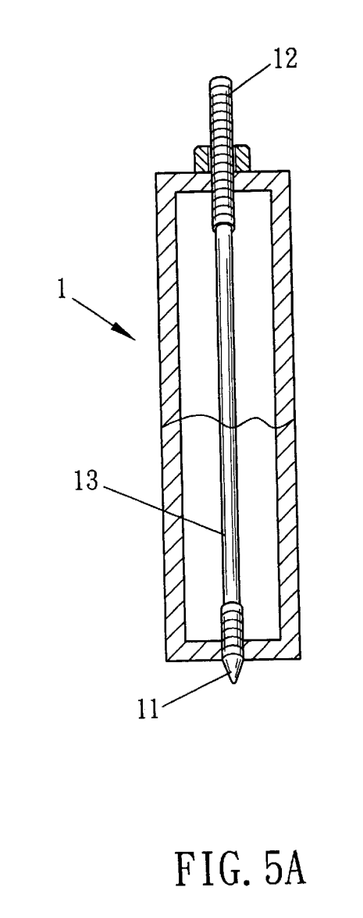
FIG. 5A is a sectional view showing the in-marrow nail of the present invention is applied to a transverse fracture.
Figure 5B:
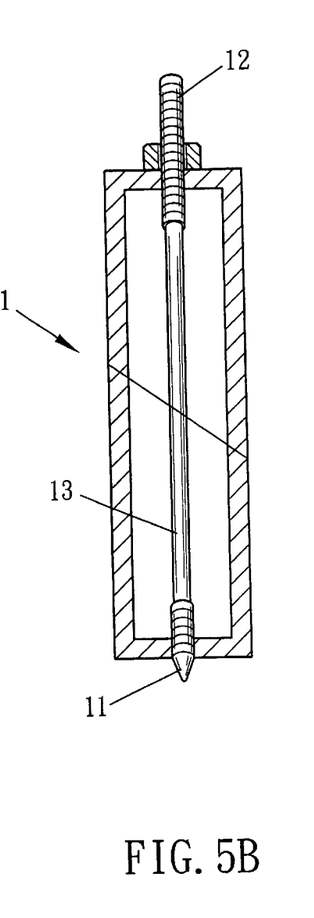
FIG. 5B is a sectional view showing the in-marrow nail of the present invention is applied to an oblique fracture.
Figure 5C:
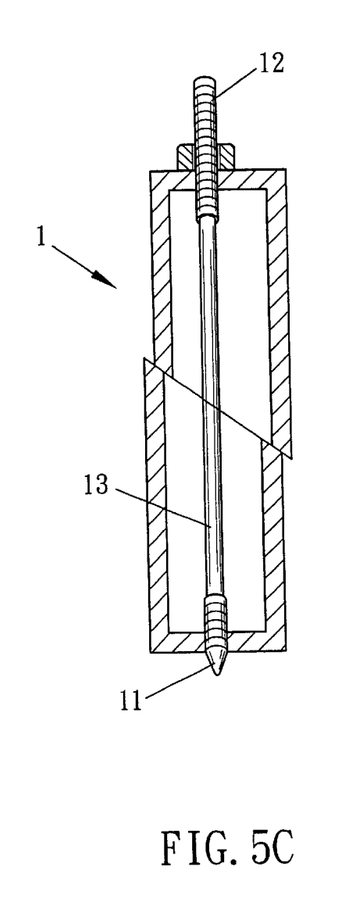
FIG. 5C is a sectional view showing the in-marrow nail of the present invention is applied to an oblique fracture in a pressurized state.

Please refer to FIG. 2. The present invention includes an in-marrow nail main body 1 two ends of which are respectively disposed with a thread tip section 11 and a thread tail section 12. A polished section 13 is formed between the two ends. A nut 2 is screwed on the thread tail section 12. The thread tip section 11 has a large thread section with larger diameter for easily drilling into and engaging with the dense section of the skeleton. The thread tip section 11 also serves to preliminarily thrust through the skeleton as shown in FIGS. 3A and 3B. In addition, when pressurized by the nut 2, the middle polished section 13 achieves a compressing and locating effect during displacement so as to enhance the firmly fixing effect. The length of the polished section 13 occupies a larger part of the total length so that the effective axial length of the in-marrow nail main body 1 is increased. When passed through the marrow, the polished section 13 is easier to be align with the fractured portion of the skeleton. Therefore, in practical application, it is avoided that the fractured portion of the skeleton is aligned with the thread section to suffer concentrated stress. Therefore, the stress is evenly distributed over the entire main body 1. In addition, the diameter of the thread tail section 12 of the main body 1 is slightly larger than the diameter of the polished section 13, while smaller than the diameter of the thread tip section 11. Therefore, the thread tip section 11 can directly preliminarily thrust through the marrow without using any other tool so that the operation time is shortened. After located, the nut 2 screwed on the thread tail section 12 is locked in to achieve an auxiliary locating effect. By means of gradually locking in the nut 2, the distal fractured skeleton is slightly slided toward the proximal section so as to effectively pressurize the fractured skeleton. Therefore, a very high stability is achieved and the unnecessary left or right displacement is minimized so as to achieve a stably fixing effect.

Referring to FIGS. 3A to 3E, in operation, the skin is first cut off and then minimum periosteum of the broken end of the clavicle is removed by a certain distance. The large thread of the thread tip section 11 of the main body 1 is used to drill and grind inside the distal marrow 4. With the same measure, the drilling and grinding are performed inside the proximal marrow 4 in reverse direction. A pneumatic drill is reversely hit into the distal section to clamp the thread tail section 12 and slowly retreat, making the thread tip section 11 slightly protrude out of the broken end of the fractured skeleton. Simultaneously, the fractured skeleton is totally restored to its home position and tightly clamped by a skeleton holder. Then the in-marrow nail main body 1 is slowly turned into the drilled marrow 4 until the thread tip section 11 slightly thrusts through the dense section of the proximal fractured skeleton. Finally, a wrench is used to firmly pressurize and tighten the nut 2 so as to achieve a pressurizing effect. Then the excessive tail section 12 behind the nut 2 by about 2 mm is cut off. It should be noted that the diameter of the drilled hole of the distal fractured skeleton is larger than the diameter of the thread tip section 12 so that during pressurizing procedure, following the trend of pressurizing, the distal fractured skeleton is displaced and pressed toward the proximal fractured skeleton. Therefore, a more firmly restoring and fixing effect is provided for the fractured skeleton so as to shorten the recovering time and achieve a good curing effect.

Referring to FIGS. 4 and 5A to 5C, when the present invention is thrust into and located in the marrow 4, the part thrusting into the marrow 4 is mostly the polished section 13. Therefore, the fractured section of the marrow is surely aligned with the polished section 13 rather than the thread section. Therefore, the breakage due to the concentrated stress taking place on the diameter variation section can be avoided and thus the shortcoming of the conventional in-marrow nail is eliminated.

The above embodiment is only used to illustrate the present invention, not intended to limit the scope thereof. Many modifications of the above embodiment can be made without departing from the spirit of the present invention.

What is claimed is:

1. An in-marrow nail structure for screwing into a fractured skeleton; said in-marrow nail structure comprising a thread tip section at a first end of said nail; a thread tail section at a second end of said nail; a polished section between said thread tip section and said thread tail section; and a nut screwed onto said thread tail section;

wherein a length of the polished section occupies a larger part of the total length of said in-marrow nail and the thread tip section, the thread tail section and the polished section each have a diameter and the diameters of the thread tip section and thread tail section are slightly larger than the diameter of the polished section.

2. The in-marrow nail structure of claim 1 wherein the thread tail section and thread tip section each has a diameter and the diameter of the thread tail section is slightly smaller than the diameter of the thread tip section.

* * * * *